(12) United States Patent
Perrey et al.

(10) Patent No.: US 9,480,403 B2
(45) Date of Patent: Nov. 1, 2016

(54) MEDICAL IMAGING SYSTEM AND METHOD FOR GENERATING A BLENDED CINE LOOP

(71) Applicants: General Electric Company, Schenectady, NY (US); n22 e.U., Wiener Neustadt (AT)

(72) Inventors: Christian Perrey, Mondsee (AT); Daniel Buckton, Salzburg (AT); Dieter Hoenigmann, Wiener Neustadt (AT)

(73) Assignees: General Electric Company, Schenectady, NY (US); E.U., N22, Wiener Neustadt (AT)

( * ) Notice: Subject to any disclaimer, the term of this patent is extended or adjusted under 35 U.S.C. 154(b) by 356 days.

(21) Appl. No.: 14/107,895

(22) Filed: Dec. 16, 2013

(65) Prior Publication Data

US 2015/0164330 A1    Jun. 18, 2015

(51) Int. Cl.
| | | |
|---|---|---|
| *A61B 8/00* | (2006.01) | |
| *A61B 5/00* | (2006.01) | |
| *A61B 8/08* | (2006.01) | |
| A61B 5/0402 | (2006.01) | |
| A61B 6/03 | (2006.01) | |
| A61B 6/00 | (2006.01) | |
| A61B 5/055 | (2006.01) | |

(52) U.S. Cl.
CPC ............ *A61B 5/0044* (2013.01); *A61B 6/463* (2013.01); *A61B 8/0866* (2013.01); *A61B 8/463* (2013.01); *A61B 8/5284* (2013.01); *A61B 5/0402* (2013.01); *A61B 5/055* (2013.01); *A61B 5/7425* (2013.01); *A61B 6/032* (2013.01); *A61B 6/503* (2013.01); *A61B 8/481* (2013.01)

(58) Field of Classification Search
CPC .. A61B 5/0044; A61B 8/0866; A61B 8/463; A61B 8/5284; A61B 6/463; A61B 8/481; A61B 5/055; A61B 6/032; A61B 6/503; A61B 5/0402; A61B 5/7425
See application file for complete search history.

(56) References Cited

U.S. PATENT DOCUMENTS

| | | | |
|---|---|---|---|
| 6,224,552 B1 * | 5/2001 | Jago | A61B 8/00 600/437 |
| 6,447,450 B1 | 9/2002 | Olstad | |
| 6,641,536 B2 | 11/2003 | Hossack et al. | |
| 8,131,041 B2 | 3/2012 | Ter Mors | |
| 8,364,244 B2 | 1/2013 | Angelos et al. | |
| 2007/0127797 A1 * | 6/2007 | Angelos | A61B 6/032 382/128 |
| 2009/0180555 A1 * | 7/2009 | Sun | H04N 7/26058 375/240.29 |
| 2012/0314945 A1 * | 12/2012 | Cha | G06T 3/4038 382/167 |

* cited by examiner

*Primary Examiner* — Jonathan Cwern (57) ABSTRACT

An medical imaging system and method for generating and displaying a blended cine loop. The system and method include acquiring image data and identifying a base image sequence in the image data. The system and method include identifying at least one non-base image in the image data acquired from outside of the base image sequence and generating a blended image sequence from the base image sequence and the at least one non-base image. The system and method include displaying the blended image sequence as a blended cine loop on a display device.

24 Claims, 7 Drawing Sheets

MEDICAL IMAGING SYSTEM AND METHOD FOR GENERATING A BLENDED CINE LOOP

FIELD OF THE INVENTION

This disclosure relates generally to a medical imaging system and a method for generating and displaying a blended cine loop with reduced artifacts.

BACKGROUND OF THE INVENTION

In clinical settings, it is known to display medical imaging data as a cine loop. For example, it is common to acquire and display ultrasound data as 2D or 3D cine loops. The cine loops are typically used to show the motion of a periodically moving object such as an adult or fetal heart. Cine loops are typically played back as "endless loops." It is extremely common for cine loops to include at least one of a spatial discontinuity or a phase discontinuity at a seam in the cine loop where cine loop transitions from an end of an image sequence to a beginning of the image sequence. These discontinuities originate from a variety of causes including irregular periodic motion of the structure being imaged, patient motion during the acquisition of the data, and any mismatch between the intended phase and the phase that was actually acquired.

Any discontinuities in the cine loop will result in an artifact that is visible to a clinician viewing the cine loop. These artifacts are distracting to the clinician and, in severe cases, could even lead to an improper diagnosis. For these and other reasons an improved method and medical imaging system for generating and displaying cine loops with reduced artifacts is desired.

BRIEF DESCRIPTION OF THE INVENTION

The above-mentioned shortcomings, disadvantages and problems are addressed herein which will be understood by reading and understanding the following specification.

In an embodiment, a method of medical imaging includes acquiring image data of a periodically moving structure over more than a single physiological cycle. The image data includes a plurality of images. The method includes associating phase information from the physiological cycle with the image data. The method includes identifying a base image sequence from the image data based on the phase information, where the base image sequence corresponds to an integral number of cycles. The method includes identifying at least one non-base image in the image data acquired from outside the base image sequence. The method includes generating a blended image sequence from the base image sequence and the at least one non-base image. The blended image sequence corresponds to the integral number of physiological cycles. The blended image sequence exhibits at least one of a reduced phase discontinuity and a reduced spatial discontinuity when displayed as a blended cine loop compared to a non-blended cine loop based on only the base image sequence. The method includes displaying the blended image sequence as a blended cine loop on a display device.

In an embodiment, a method of medical imaging includes acquiring image data of a periodically moving structure over more than a single physiological cycle, the image data including a plurality of images. The method includes associating phase information from the physiological cycle with the image data and identifying a base image sequence from the image data corresponding to an integral number of physiological cycles. The base image sequence includes first and second base images with associated first and second phases. The method includes identifying first and second non-base images acquired from outside the base image sequence in the image data. The first non-base image represents the first phase and the second non-base image represents the second phase. The method includes blending the first and second non-base images with the base image sequence using a first weighting function for combining the first base image with the first non-base image and a second weighting function for combining the second base image with the second non-base image in order to generate a blended image sequence corresponding to the integral number of cycles. The method also includes displaying the blended image sequence as a blended cine loop on a display device.

In another embodiment, a medical imaging system includes an acquisition device, a display device, and a processor in electronic communication with the acquisition device and the display device. The processor is configured to control the acquisition device to acquire image data of a periodically moving structure over more than a single physiological cycle. The processor is configured to associate phase information from the physiological cycle with the image data. The processor is configured to identify a base image sequence from the image data based on the phase information, where the base image sequence corresponds to an integral number of cycles. The processor is configured to identify at least one non-base image in the image data acquired from outside the base image sequence. The processor is configured to generate a blended image sequence corresponding to the integral number of physiological cycles from the base image sequence and the at least one non-base image. Wherein the blended image sequence exhibits at least one of a reduced phase discontinuity and a reduced spatial discontinuity when displayed as a blended cine loop compared to a non-blended cine loop based on only the base image sequence. The processor is configured to display the blended image sequence as a blended cine loop on the display device.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
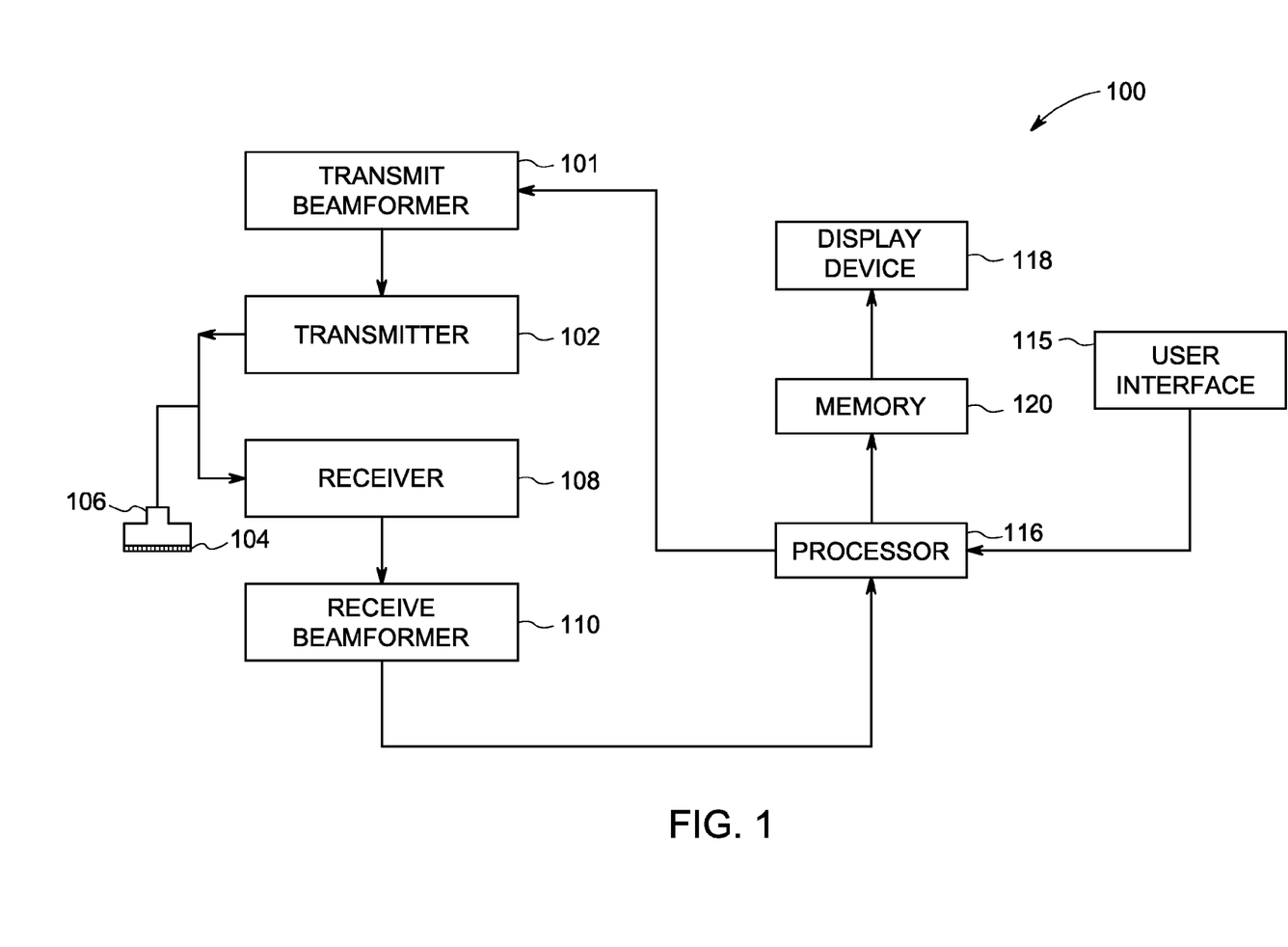
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within a probe 106 to emit pulsed ultrasonic signals into a body (not shown). The probe 106 may be an 2D array probe according to an embodiment. However, any other type of probe may be used according to other embodiments. The pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 101, the transmitter 102, the receiver 108 and the receive beamformer 110 may be situated within the probe 106. The terms "scan" or "scanning" may also be used in this disclosure to refer to acquiring data through the process of transmitting and receiving ultrasonic signals. The terms "data" or "ultrasound data" may be used in this disclosure to refer to either one or more datasets acquired with an ultrasound imaging system. A user interface 115 may be used to control operation of the ultrasound imaging system 100, including the input of patient data and/or the selection of scanning or display parameters.

The ultrasound imaging system 100 also includes a processor 116 to control the transmit beamformer 101, the transmitter 102, the receiver 108 and the receive beamformer 110. The processor 116 is in electronic communication with the probe 106. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. For purposes of this disclosure, the term "electronic communication" may be defined to include both wired and wireless connections. The processor 116 may include a central processor (CPU) according to an embodiment. According to other embodiments, the processor 116 may include other electronic components capable of carrying out processing functions, such as a digital signal processor, a field-programmable gate array (FPGA) or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation may be carried out earlier in the processing chain. The processor 116 may be adapted to perform one or more processing operations on the data according to a plurality of selectable ultrasound modalities. The data may be processed in real-time during a scanning session as the echo signals are received. For the purposes of this disclosure, the term "real-time" is defined to include a procedure that is performed without any intentional delay. For example, an embodiment may acquire and display data a real-time frame-rate of 7-50 frames/sec. For purposes of this disclosure, the term "frame-rate" may be applied to either 2D or 3D frames of ultrasound data. Additionally, the term "volume-rate" may be used to refer to the frame-rate when applied to 4D ultrasound data. It should be understood that the real-time frame rate may be dependent on the length of time that it takes to acquire each volume of data. For a volume acquisition, frame rate depends on the length of time required to acquire each volume of data. Accordingly, when acquiring a relatively large volume of data, the real-time volume-rate may be slower. Thus, some embodiments may have real-time volume-rates that are considerably faster than 50 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the data may be refreshed at a similar volume-rate. Other embodiments may acquire and display data at different rates. For example, some embodiments may acquire data at a volume-rate of less than 10 Hz or greater than 30 Hz depending on the size of the volume and the intended application. A memory 120 is included for storing processed frames of acquired data. In an exemplary embodiment, the memory 120 is of sufficient capacity to store at least several seconds worth of frames of ultrasound data. The frames of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or frames are stored and timing information indicating a time at which the data was acquired in memory may be recorded. The modules may include, for example, a scan conversion module to perform scan conversion operations to convert the image frames from beam space coordinates to display space coordinates. A video processor module may be provided that reads the image frames from a memory and displays the image frames in real-time while a procedure is being carried out on a patient. A video processor module may store the image frames in an image memory, from which the images are read and displayed.

Figure 2:
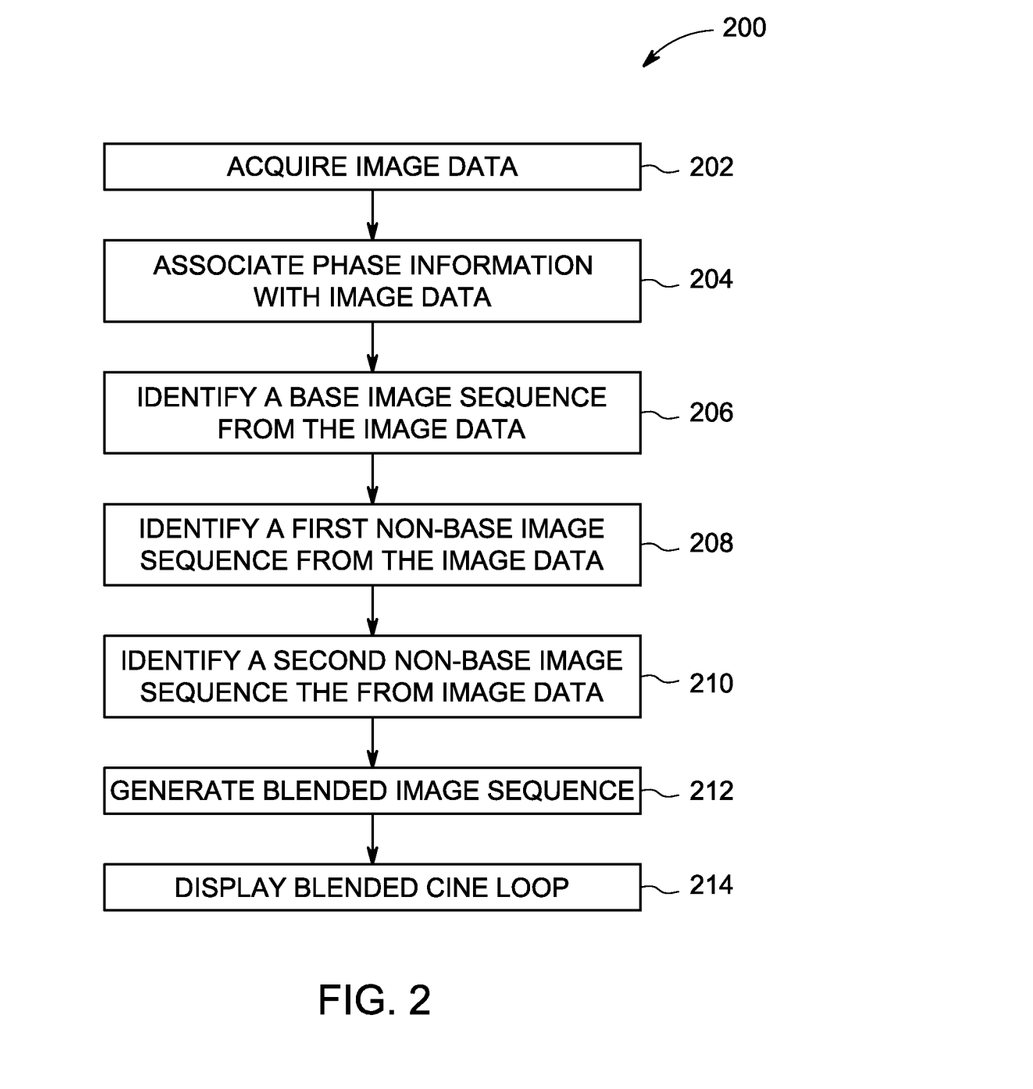
FIG. 2 is a flow chart of a method in accordance with an embodiment.

FIG. 2 is a flow chart of a method in accordance with an exemplary embodiment. The individual blocks of the flow chart represent steps that may be performed in accordance with the method 200. Additional embodiments may perform the steps shown in a different sequence and/or additional embodiments may include additional steps not shown in FIG. 2. The technical effect of the method 200 is the display of a blended cine loop. The method 200 will be described according to an exemplary embodiment where the method 200 is implemented with the ultrasound imaging system 100 of FIG. 1 and the image data comprises ultrasound data. However, it should be appreciated that, according to other embodiments, the method 200 may be implemented with medical imaging systems from different modalities including X-ray imaging systems, computed tomography (CT) imaging systems, magnetic resonance imaging (MRI) systems, or any other imaging system capable of acquiring image data that could be displayed as a cine loop. Since the method 200 will be described according to an embodiment where the imaging system is an ultrasound imaging system, the image data will comprise ultrasound data. Additionally, the method 200 will be described according to an embodiment where 4D ultrasound data of a fetal heart is acquired. It should be appreciated that according to other embodiments, the method 200 may be used to display 2D or 4D ultrasound data acquired from other structures including some or all of an adult heart and/or a carotid artery.

Referring to FIGS. 1 and 2, at step 202 the processor 116 controls the transmit beamformer 101, the transmitter 102, the probe 106, the receiver 108, and the receive beamformer 110 to acquire ultrasound data. The processor 116 controls the components of the ultrasound imaging system 100 to acquire ultrasound data for longer than a complete physiological cycle. The method 200 will be described according to an exemplary embodiment where the ultrasound data comprises data of a heart and the physiological cycle comprises a cardiac cycle, but it should be appreciated that other embodiments may acquire ultrasound data of different periodically moving structures. Additionally, the periodically moving structures may move according to a different physiological cycle such as a respiratory cycle. A clinician may determine the length of the acquisition of ultrasound data at step 202, or the processor 116 may determine the duration of the acquisition data based on data from a device connected to the patient and adapted to determine phase information about the patient's physiological cycle. According to an exemplary embodiment, an ECG machine (not shown) may be connected to the patient and ECG data may be provided to the processor 116.

According to an embodiment, ultrasound data may be acquired for just slightly longer than a cardiac cycle. For example, the acquisition may be longer than the cardiac cycle by just a single image, or the acquisition of ultrasound data at step 202 may exceed the length of the cardiac cycle by multiple images. According to an exemplary embodiment, the acquisition of ultrasound data at step 202 may exceed the length of the cardiac cycle by two or more images.

Figure 3:
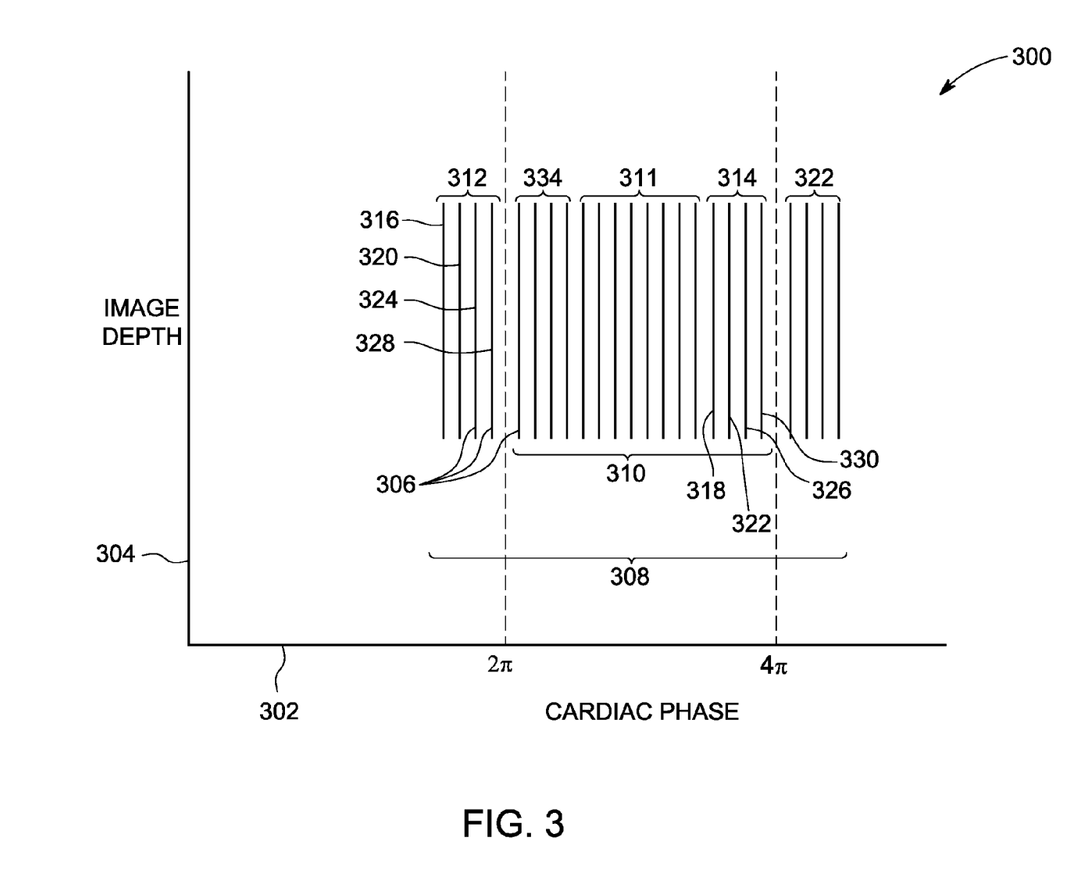
FIG. 3 is a schematic representation of an acquisition of ultrasound data in accordance with an exemplary embodiment.

FIG. 3 is a schematic representation of an acquisition 300 of image data according to an embodiment. The image data in FIG. 3 will be described according to an exemplary embodiment where the image data is ultrasound data, but image data from other modalities may be used according to other embodiments. Axis 302 represents cardiac phase, while axis 304 represent image depth. Each vertical line 306 represents an image. Ultrasound data 308 includes a plurality of images acquired over longer than a cardiac cycle as illustrated by the heart phase information on axis 302. FIG. 3 illustrates that the acquisition of ultrasound data 308 was started before a cardiac phase of $2\pi$ and extends until a cardiac phase after $4\pi$, which is longer than one complete cardiac cycle.

Referring to FIGS. 1, 2, and 3, at step 204, the processor 116 associates phase information with the ultrasound data 308. As discussed previously, the phase information may be acquired at the same time that the ultrasound data is acquired. That is, phase information from an external device such as an ECG machine may be acquired from the patient at the same time as the ultrasound data is acquired during step 202. According to other embodiments, image processing techniques may be applied to the ultrasound data 308 in order to detect the phase of each image 306 in the ultrasound data. For example, the image processing technique may focus on a portion of the heart where movements correspond to phase, such as one or more heart valves. According to other embodiments, a Fourier analysis may be applied to the ultrasound data 308 in order to estimate the phase of each image 306 in the ultrasound data 308. According to yet another embodiment, one or more M-mode lines (not shown) may be interleaved with the acquisition of the ultrasound data 308. The M-mode lines may intersect a portion of a structure such as a valve that clearly exhibits periodic motion. The phase of each image 306 may then be determined based on the M-mode data. The above examples represent only a limited number of all the techniques that may be used to determine phase. It should be appreciated that additional techniques of determining or estimating the phases of images within the ultrasound data may also be used.

Still referring to FIGS. 1, 2, and 3, at step 206 of the method 200 a base image sequence 310 is identified from the ultrasound data 308. The base image sequence 310 may be identified based on operator input, or the base image sequence 310 may be automatically identified by the processor 116 based on the phase information associated with the ultrasound data 308 at step 204. The base image sequence 310 represents an integral number of cardiac cycles according to an exemplary embodiment. The base image sequences may represent other physiological cycles according to other embodiments. In FIG. 3, the base image sequence 310 starts at $2\pi$ and extends to $4\pi$, making it exactly one heart cycle in length. According to other embodiments, a base image sequence may be selected that does not start exactly at the start of a physiological cycle. For example, in other embodiments, the base image sequence may start at any phase of the physiological cycle as long as the base image sequence represents an integral number of cardiac cycles. The base image sequence may represent any integral number of cardiac cycles in other embodiments.

At step 208, the processor 116 identifies a first non-base image sequence 312 from the ultrasound data 308. The first non-base image sequence 312 is less than a complete cardiac cycle in length. The first non-base image sequence 312 was acquired before the base image sequence 310. However, according to other embodiments, a non-base image sequence may be acquired after the base image sequence 310. The images in the first non-base image sequence 312 correspond to the images in a first subset 314 of the base image sequence 310. For example: non-base image 316 is the same phase as base image 318; non-base image 320 is the same phase as base image 322; non-base image 324 is the same phase as base image 326; and non-base image 328 is the same phase as base image 330.

At step 210, a second non-base image sequence 322 is identified by the processor 116. The second non-base image sequence 322 is identified from the ultrasound data 308 and was acquired after the base image sequence 310. According to other embodiments, the second non-base image sequence 322 may be acquired before the base image sequence 310. The second non-base image sequence 322 corresponds to a second subset 334 of the base image sequence 310. Both the second non-base image sequence 322 and the second subset 334 include the same number of images, and the images in the second non-base image sequence 322 are phase-matched to the second subset 334. The term "phase-matched" is defined to include a pair of images acquired from different physiological cycles that both represent the same physiological phase. In the exemplary embodiment shown in FIG. 3, the first subset 314, the second subset 334, the first non-base image sequence 312 and the second non-base image sequence 322 are each comprised of four images. However, it should be appreciated that any pair of corresponding image sequences may include a different number of images. For example, a first pair of corresponding image sequences, namely the first non-base image sequence 312 and the first base image sequence 314, could include either more than four images or fewer than four images. According to another embodiment where the base image sequence 310 is more than one physiological cycle, additional data from within the base image sequence may be used to generate the blended image sequence. For example, one or more images in the base image sequence near the start or end of the base image sequence may be blended with one or more images from a different physiological cycle within the base image sequence in order to generate a blended image sequence.

At step 212 of the method 200, the processor 116 generates a blended cine loop from the base image sequence 310, the first non-base image sequence 312 and the second non-base image sequence 322. The processor 116 blends the data from the base image sequence 310 with the first subset 314, and the processor 116 blends the data from the second non-base image sequence 322 with the second subset 334. The ultrasound data is blended based on phase. For example: non-base image 316 and base image 318 have common phases; non-base image 320 and base image 322 both have common phases; images non-base image 324 and base image 326 have common phases; and non-base image 328 and base image 330 have common phases. As such, images 316 and 318 are blended together, images 320 and 322 are blended together, and images 328 and 330 are blended together. The second non-base image sequence 322 may also be blended with the base image sequence 310. According to the embodiment shown in FIG. 3, the second non-base image sequence 322 may be blended with the second subset 334.

On or more weighting functions may be used to control the relative contribution of the base image and the corresponding non-base image towards the resulting blended image. An exemplary weighting function is listed below:

$$\text{Image}_{Blended} = W_1 * \text{Image}_{Base} + W_2 * \text{Image}_{Non\text{-}base}$$

Where $\text{Image}_{Blended}$ is a blended image, $W_1$ is a first weight, $\text{Image}_{Base}$ is a base image, $W_2$ is a second weight, and $\text{Image}_{Non\text{-}base}$ is a non-base image. The values assigned to $W_1$ and $W_2$ may be adjusted to control the relative contribution of the base image and the non-base image to the resulting blended image. For purposes of this disclosure two weighting functions with at least one different value for either the first weight or the second weight will be considered to be different weighting functions since they will results different relative contributions of the base image and the non-base image. Other embodiments may use different weighting functions.

Figure 4:
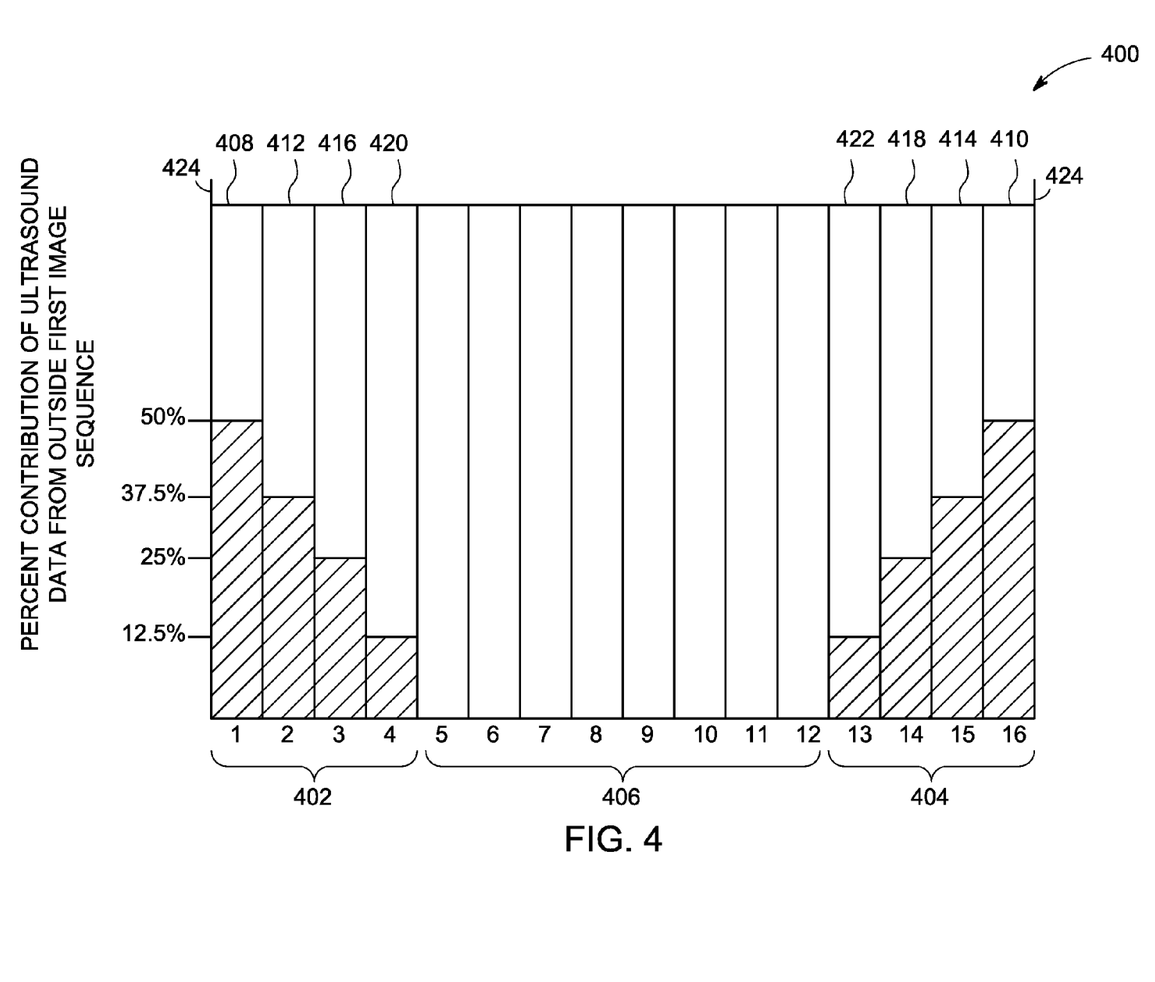
FIG. 4 is a schematic representation of a blended image sequence generated in accordance with an embodiment.

FIG. 4 is a schematic representation of a blended image sequence 400 that, according to an exemplary embodiment, is generated according to the method 200 described with respect to FIGS. 2 and 3. The blended image sequence 400 may be based on image data from any imaging modality according to other embodiments. The blended image sequence 400 may be displayed as a blended cine loop by repeatedly displaying the images in the blended image sequence 400. There are 16 numbered columns in FIG. 4. Each column represents an image in the blended image sequence 400. The blended image sequence 400 is an example of a blended image sequence 400 that would be generated at step 212 of the method 200. The blended image sequence includes a first set of blended images 402 at the start of the blended image sequence 400 and a second set of blended images 404 at the end of the blended image sequence 400. The blended image sequence 400 includes a seam 424. The seam 424 is the location in the blended image sequence 400 where the blended image sequence 400 transitions from the end to the start when displayed as a blended cine loop. In other words, when displayed as a blended cine loop, the image sequence 400 progresses from image 16 to image 1 at the seam 424. So, the seam 424 represents the location where the blended cine loop transitions from image 410, which is at the end of the blended image sequence 400, to image 408, which is at the start of the blended image sequence 400. The start is defined to be the portion of the blended image sequence 400 that is displayed immediately after the seam 424, while the end is the portion of the blended image sequence 400 that is displayed immediately before the seam 424. The blended image sequence 400 includes an unblended portion 406 as well. It should be appreciated that according to other embodiments, the blended images may only be at one of the start and the end of the blended image sequence 400. Embodiments may include a different number of blended images. For example, embodiments may blend either more than four images in an image sequence together or less than four images in an image sequence together. Some embodiments may include blending only a two images together to generate a single blended image that is part of a blended images sequence.

Referring to FIG. 4, each column represents an image in the blended image sequence 400. The relative contribution of the base images and the corresponding non-base images to the blended cine loop is also represented in FIG. 4. Images 408 and 410 are generated using the first weighting function. The base image contributes 50% to the blended image and the non-base image contributes 50% to the blended image according to an exemplary first weighting function below:

$$Image_{Blended} = 0.5 * Image_{Base} + 0.5 * Image_{Non-base}$$

Blended images 412 and 414 are both generated with a weighting function emphasizing the base image more strongly than the non-base image. Images 412 and 414 are generated using a second weighting function. The base image contributes 62.5% to the blended image and the non-base image contributes 37.5% to the blended image according to an exemplary second weighting function below:

$$Image_{Blended} = 0.625 * Image_{Base} + 0.375 * Image_{Non-base}$$

Blended images 416 and 418 are both generated with an embodiment emphasizing the base image more strongly than the non-base image. Images 416 and 418 are generated using the third weighting function. The base image contributes 75% to the blended image and the non-base image contributes 25% to the blended image according to an exemplary third weighting function below:

$$Image_{Blended} = 0.75 * Image_{Base} + 0.25 * Image_{Non-base}$$

Blended images 420 and 422 are both generated with an embodiment emphasizing the base image more strongly than the non-base image. Images 420 and 422 are generated using the fourth weighting function. The base image contributes 87.5% to the blended image and the non-base image contributes 12.5% to the blended image according to an exemplary fourth weighting function below:

$$Image_{Blended} = 0.875 * Image_{Base} + 0.125 * Image_{Non-base}$$

The first weight and the second weight add up to 1 for each of the weighting functions described hereinabove. It should be appreciated that different weighting functions may be used for other embodiments. The blended image sequence 400 shown in FIG. 4 depicts that the weighting functions vary in a linear manner based on the distance of the blended image from the seam 424. While the concept of the seam makes the most sense with respect to a blended cine loop, it is displayed on the blended image sequence since the blended cine loop involves repeatedly playing the blended image sequence 400. The concept and location of the seam may be used with respect to either a blended image sequence or a blended cine loop in this disclosure.

In the exemplary blended image sequence 400 the weighting functions applied to the blended image sequences 402 and 404 vary based on distance of the blended image from the seam 424. Blended images close to the seam 424, like 408 and 410, may emphasize the non-base image more strongly. Meanwhile, images further from the seam 424, such as 420 and 422, may emphasize the non-base image less strongly than the base image. In FIG. 4, the weighting functions vary in a linear manner based on distance from the seam 424. However, it should be appreciated that the weighting functions may be adjusted in a different manner in other embodiments. Different weighting functions may be used based on the position of the blended images with respect to the seam 424 in order to generate a smoother transition when displayed as a blended cine loop. Blended images close to the seam, like 408 and 410 may emphasize the non-base image more strongly in order to increase the likelihood of a smooth transition between the last image 410 in the blended image sequence 400 and the first image 408 in the blended image sequence 400. It may be advantageous to decrease the contribution of the non-base images to the blended images further from the seam 424 in order to more smoothly transition to the unblended portion 406 of the blended image sequence 400. If there is too abrupt of a transition from an image with a strong contribution from the non-base image to an image with a strong contribution from the base-image, there is a risk of adding an additional artifact due to this transition. Additional, the weighting functions may be selected to result in different types of transitions. As discussed previously, the weighting functions adjust the relative contribution of the base image and the non-base in a linear transition in the blended image sequence base on distance from the seam 424. Other embodiments may select the weighting functions differently in order to result in different types of transitions including exponential or quadratic transitions based on distance from the seam 424.

Referring back to FIG. 2, an additional step may be performed before generating the blended image sequence between step 210 and 212. The processor 116 (shown in FIG. 1) may calculate a correlation between a base image and a corresponding non-base image. The processor 116 may select the weighting function used to blend individual images together based on a correlation of a base image selected from the base image sequence 310 (shown in FIG. 3) to a non-base image, selected from either the first non-base image sequence 312 (shown in FIG. 3) or the second non-base image sequence 322 (shown in FIG. 3). The processor 116 may then select the weighting function based on the correlation of the corresponding images. If the corresponding images are strongly correlated, then the processor 116 may assign a weighting function that emphasizes the non-base image relatively strongly in the blended image. However, if the corresponding images are not strongly correlated, it would tend to indicate that the structure of interest had moved from one physiological cycle to the next. This could be due to either patient motion or an irregularity in the patient's physiological cycle. If the corresponding images are not strongly correlated, it would not be beneficial to emphasize the non-base image as strongly in a blended image. As such, the processor 116 may assign a weighting function where the non-base image is not strongly emphasized or where the non-base image is completely excluded from the final cine loop. The processor 116 may calculate a correlation for each pair of corresponding images and select the most appropriate weighting function based on the strength of the correlation. The processor 116 may also select the weighting function for each pair of corresponding images based on multiple factors. For example, the processor 116 may rely on both the position of the blended image from the seam 424 (shown in FIG. 4) and the strength of the correlation. These are just two exemplary variables that could be analyzed by the processor 116 when selecting weighting functions. It should be appreciated that the processor 116 may use additional variables when selecting the weighting function used to generate each blended image in the blended cine loop.

Referring back FIG. 2, at step 214 the processor 116 displays the blended image sequence 400 as a blended cine loop. As discussed previously, the blended cine loop may be generated by displaying the blended image sequence 400 as a loop joined at the seam 424. The blended cine loop will continuously cycle through the images in the blended image sequence 400 for either a present number of cycles or until the clinician decides to stop the displaying of the blended cine loop.

By basing the blended cine loop on the blended image sequence 400 instead of on just the base image sequence 310 (shown in FIG. 3), the blended cine loop has a smoother transition at the seam 424. Blending additional images from outside the base image sequence 310 make the images close to the seam 424 of sequence 400 more representative of a structure during an average physiological cycle. Blending reduces the effects of any irregularities or unwanted patient motion that occurred during the base image sequence 308. Additionally, in the embodiment shown in FIG. 3, the non-base ultrasound images were acquired right before and after the base image sequence 308. A blended cine loop based on data blended in the manner described hereinabove will minimize the effects of any differences between the end of the base image sequence 310 and the start of the base image sequence 310.

Figure 5:
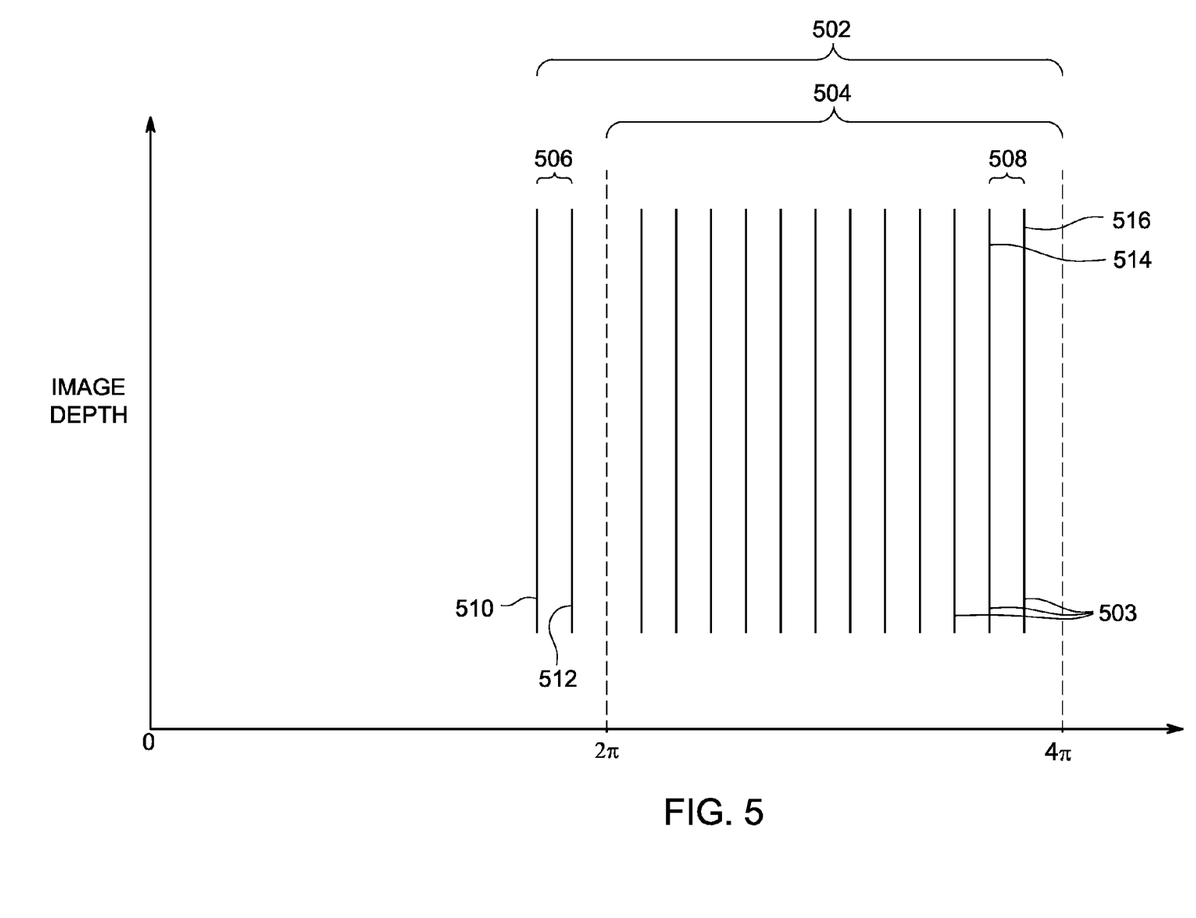
FIG. 5 is a schematic representation of an acquisition of ultrasound data in accordance with an exemplary embodiment.

FIG. 5 is a schematic representation of an acquisition of ultrasound data in accordance with an exemplary embodiment. Ultrasound data 502 is represented by a plurality of vertical lines 503. Each vertical line represents an image just like in previously described FIG. 3. A base image sequence 504 extends from $2\pi$ to $4\pi$ and represents images acquired during a complete cardiac cycle. A non-base image sequence 506 includes two images that were acquired before the first image sequence 504. The first non-base image sequence 506 includes a first non-base image 510 and a second non-base image 512. The first image sequence 506 includes a first base image 514 and a second base image 516. The first non-base image 510 corresponds to the first base image 514 and the second non-base image 512 corresponds to the second base image 516. Each corresponding pair of images represents the same cardiac phase. The processor 116 (shown in FIG. 1) may blend the first non-base image 510 with the first base image 514 and the second non-base image 514 with the second base image 516 in accordance with an embodiment. The processor 116 may apply a different weighting function when combining the first non-base image 510 with the first base image 514 and the second non-base image 512 with the second base image 516 to generate a blended cine loop. According to another embodiment (not shown), the processor 116 may blend a single non-base image with a corresponding base image to generate a blended image sequence. The blended image sequence may be displayed as a blended cine loop on a display device such as the display device 118 shown in FIG. 1.

Figure 6:
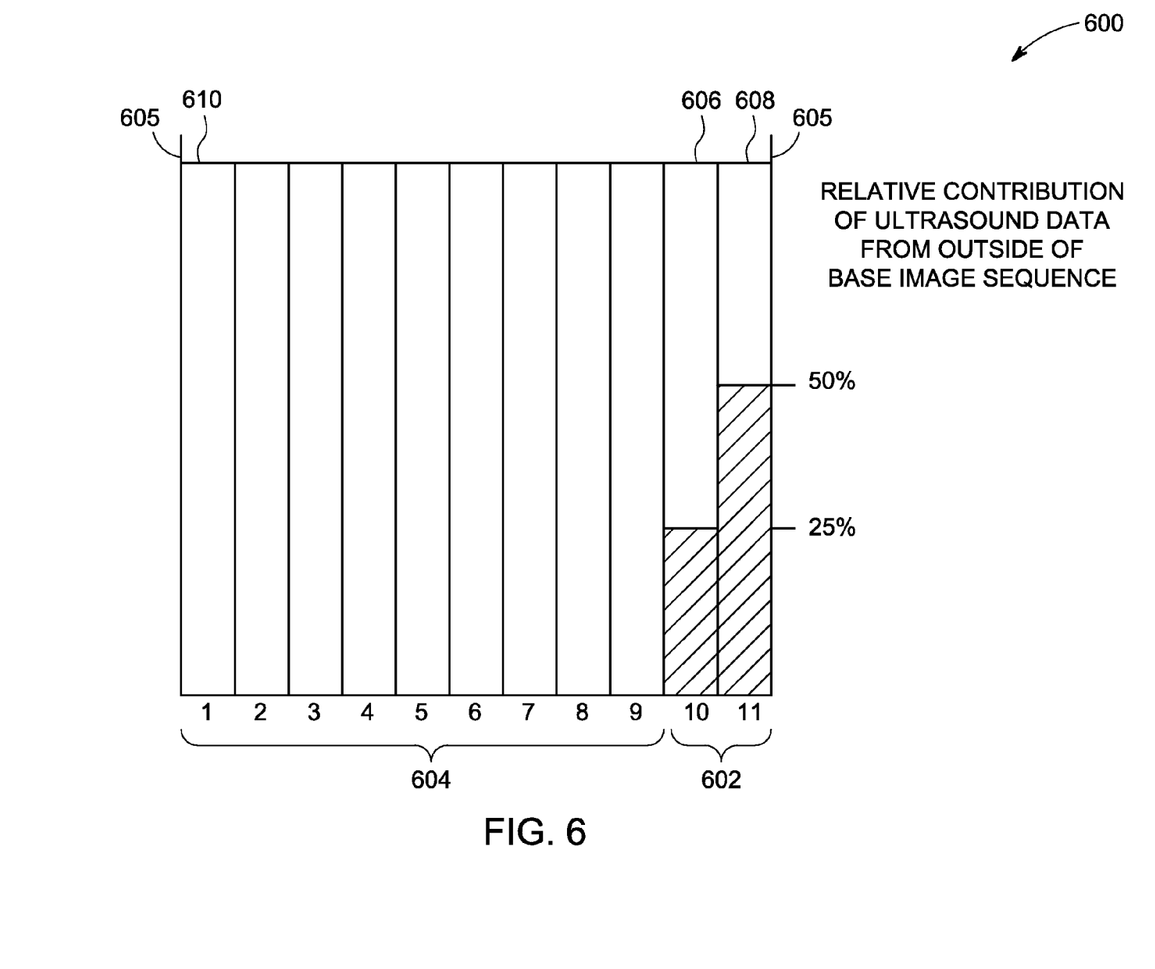
FIG. 6 is a schematic representation of a blended image sequence generated in accordance with an embodiment.

FIG. 6 is a schematic representation of a blended image sequence 600 that is generated according to an exemplary embodiment described with respect to FIG. 5. The blended image sequence 600 may be displayed as a blended cine loop by repeatedly displaying the images in the blended image sequence 600. There are 11 numbered columns in FIG. 6. Each column represents an image in the blended image sequence 600. The blended image sequence 600 includes a set of blended images 602 and an unblended portion 604. The blended image sequence 600 includes a seam 605. The seam 605 is the location in the blended image sequence 600 where the blended image sequence 600 transitions from the end to the start when displayed as a blended cine loop. In other words, when displayed as a blended cine loop, the image sequence 600 progresses from image 11 to image 1 at the seam 605. So, the seam 605 represents the location where the blended cine loop transitions from the image 608, which is at the end of the blended image sequence 600, to image 610, which is at the start of the blended image sequence 400.

Still referring to FIG. 6, each column represents an image in the blended image sequence. The relative contribution of the base images and the corresponding non-base images to the blended cine loop is also represented in FIG. 6. Blended image 608 is generated according to a weighting function where the base image contributes 50% to the blended image and the non-base image contributes 50% to the blended image according to an exemplary first weighting function below:

$$\text{Image}_{Blended}=0.5*\text{Image}_{Base}+0.5*\text{Image}_{Non-base}$$

Blended image 606 is generated according to a weighting function where the base image is weighted more strongly than the non-base image. Image 606 is generated using a second weighting function. The base image contributes 75% and the non-base image contributes 25% according to an exemplary second weighting function below:

$$\text{Image}_{Blended}=0.75*\text{Image}_{Base}+0.25*\text{Image}_{Non-base}$$

Different weighting functions may be applied to generate the blended images according to other embodiments. Additionally, other embodiments may have a different number of blended images.

Figure 7:
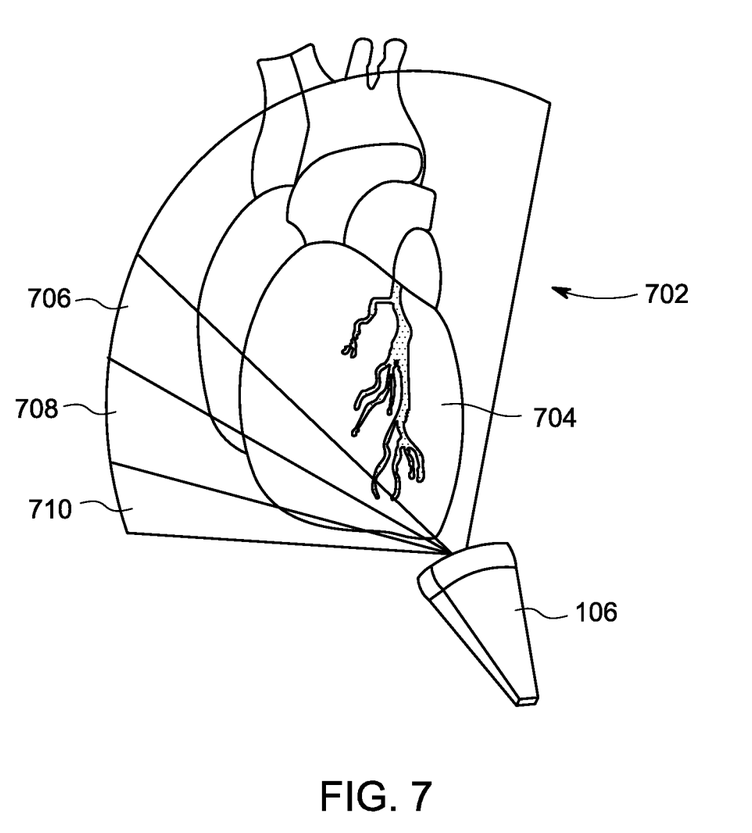
FIG. 7 is a schematic representation of a partial volume acquisition in accordance with an exemplary embodiment.

FIG. 7 is a schematic representation of a partial volume acquisition 702 in accordance with an exemplary embodiment. FIG. 6 includes the probe 106 and a heart 704. The partial volume acquisition 702 is divided into three sub-volumes: a first sub-volume 706, a second sub-volume 708, and a third sub-volume 610. According to an exemplary embodiment, the processor 116 controls the probe 106 to acquire an image sequence of each of the sub-volumes 706, 708, and 610 for longer than a cardiac cycle. The processor may use the method previously described with respect to FIGS. 2, 3, and 4 in order to individually acquire data for the first sub-volume 706, the second sub-volume 708, and the third sub-volume 610. This results in the generation of a blended image sequence for each of the sub-volumes. As previously described, the blended image sequence reduces spatial and phase discontinuities present compared to the base image sequence 310. The processor 116 then stitches the data together from the three sub-volumes to generate a single blended volume. The processor 116 combines each image based on both cardiac phase and location. The processor 116 matches images showing a common phase from the first sub-volume 706 with corresponding images from the second sub-volume 708 and the third sub-volume 610. When the processor 116 generates the blended image sequence of the whole volume 702, the processor 116 combines images both spatially and temporally. Partial volume acquisitions are particularly sensitive to image artifacts since any spatial discontinuities are readily visible at the interfaces between each of the partial volumes. Additionally, a cine loop of the final volume may have a slightly different artifact present for each of the sub-volumes when displayed as a cine loop. Therefore, using blended image sequences for each of the sub-volumes in a partial volume acquisition can significantly reduce artifacts due to spatial discontinuities between the various sub-volumes, and artifacts due to spatial and/or phase discontinuities due to seams in a cine loop.

Figure 8:
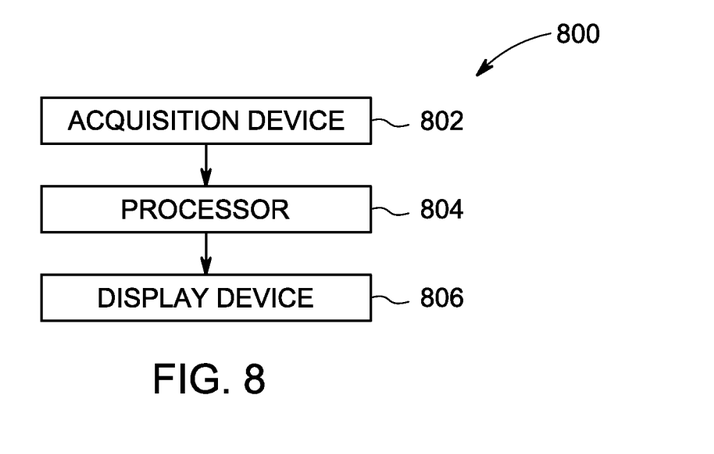
FIG. 8 is a schematic representation of a medical imaging system in accordance with an exemplary embodiment.

FIG. 8 is a schematic representation of a medical imaging system 800 in accordance with an embodiment. The medical imaging system includes an acquisition device 802, a processor 804, and a display device 806. The acquisition device 802 and the display device 806 are both in electronic communication with the processor 804. The acquisition device 802 can be a probe for embodiments where the medical imaging system 800 comprises an ultrasound imaging system. The acquisition device 802 can be an X-ray tube and an X-ray detector according to an embodiment where the medical imaging system 800 comprises an X-ray imaging system. The acquisition device 802 can be an X-ray tube and a detector array according to an embodiment where the medical imaging system 800 comprises a computed tomography imaging system. It should be appreciated by those skilled in the art that the acquisition device 802 can include other components according to additional embodiments where the medical imaging system 800 comprises a different imaging modality.

The processor 804 may be configured to control the medical imaging system 800 in a method similar to the method 200 (shown in FIG. 2). The method 200 was described hereinabove with respect to an ultrasound imaging system and ultrasound data. The processor 804 may include any processor-based or microprocessor-based system. The processor may include ASICs, microcontrollers, logic circuits, or any other circuit or processor capable of executing a set of commands or instructions. It should be appreciated that the processor 804 may be configured to perform the method 200 using data from a modality other than ultrasound. For example, the processor 804 may be configured to implement the method 200 using CT data for embodiments where the medical imaging system is a CT imaging system; the processor 804 may be configured to implement the method 200 using MRI data for embodiments where the medical imaging system is a MRI system; and the processor 804 may be configured to implement the method 200 using X-ray data for embodiments where the medical imaging system is a X-ray imaging system. The display device 806 may include a monitor, a display, an LED flat screen, an OLED screen, a projector, or any other device capable of displaying an image.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of medical imaging comprising:
acquiring image data of a periodically moving structure over more than a single physiological cycle, the image data comprising a plurality of images representing the structure at different phases of a physiological cycle;
associating phase information from the physiological cycle with the image data;
identifying a base image sequence from the image data based on the phase information, the base image sequence corresponding to an integral number of physiological cycles;
identifying a plurality of non-base images in the image data, where the plurality of non-base images were acquired either before or after the base image sequence during the process of said acquiring the image data of the periodically moving structure;
generating a blended image sequence, the blended image sequence comprising a start, an end, a set of blended images, an unblended portion, and a seam indicating a location in the blended image sequence where the blended image sequence transitions from the end to the start when the blended image sequence is displayed as a blended cine loop, where the set of blended images is generated by blending each of the plurality of non-base images with a corresponding one of the base images according to one of a plurality of weighting functions, where the weighting function used to control the blending is selected based on a distance of the blended image from the seam, where the set of blended images reduces the appearance of the seam when the blended image sequence is displayed as the blended cine loop; and
displaying the blended image sequence as the blended cine loop on a display device.

2. The method of claim 1, wherein the image data comprises ultrasound data.

3. The method of claim 1, wherein the image data comprises X-ray data or computed tomography data.

4. The method of claim 1, wherein the image data comprises magnetic resonance imaging data.

5. The method of claim 1, wherein the structure comprises either at least a portion of a heart or a carotid artery.

6. The method of claim 5, wherein the physiological cycle comprises a cardiac cycle and the phase information comprises cardiac phase information.

7. The method of claim 6, further comprising acquiring the cardiac phase information with an ECG machine during the process of said acquiring the image data.

8. The method of claim 1, wherein identifying the plurality of non-base images comprises identifying a non-base image sequence acquired before the base image sequence.

9. The method of claim 8, further comprising identifying a second non-base image sequence acquired after the base image, where the second non-base image sequence is identified from the acquired image data of the periodically moving structure, and wherein generating the blended image sequence further comprises blending the base image sequence with both the first non-base image sequence and the second non-base image sequence.

10. The method of claim 1, where the weighting functions are selected to vary in a linear manner based on distance of the blended image from the seam.

11. The method of claim 1, where the weighting functions are selected to emphasize the non-base image more strongly at a first location compared to a second location, where the first location is closer to the seam than the second location.

12. The method of claim 11, where the weighting functions are selected to emphasize the non-base image more strongly than the base image at the first location and to emphasize the base image more strongly than the non-base image at the second location.

13. A method of medical imaging comprising:
acquiring image data of a periodically moving structure over more than a single physiological cycle, the image data comprising a plurality of images representing the structure at different phases of the physiological cycle;
associating phase information from the physiological cycle with the image data;
identifying a base image sequence from the image data corresponding to an integral number of physiological cycles, the base image sequence including first and second base images with associated first and second phases;
identifying first and second non-base images in the image data, the first non-base image representing the first phase and the second non-base image representing the second phase, where the first and second non-base images were acquired either before or after the base image sequence during the process of said acquiring the image data;

generating a blended image sequence, the blended image sequence comprising a start, an end, a set of blended images, an unblended portion, and a seam indicating a location in the blended image sequence where the blended image sequence transitions from the end to the start when the blended image sequence is displayed as a blended cine loop, where generating the blended image sequence comprises blending the first non-base image with a first corresponding base image in the base image sequence according to a first weighting function to generate a first blended image and blending the second non-base image with a second corresponding base image in the base image sequence according to a second weighting function to generate a second blended image, where the set of blended images reduces the appearance of the seam when the blended image sequence is displayed as the blended cine loop, where the second weighting function is different than the first weighting function, and where at least one of the first blended image and the second blended image is adjacent to the seam; and displaying the blended image sequence as the blended cine loop on a display device.

14. The method of claim 13, wherein the weighting functions are selected based on a distance of a resulting blended image from the seam in the blended cine loop.

15. The method of claim 14, wherein the first blended image-is closer to the seam in the blended cine loop than the second blended image, and wherein the first weighting function emphasizes the first non-base image more strongly than the second weighting function emphasizes the second non-base image.

16. The method of claim 13, further comprising selecting a value for the first weighting function based on a level of similarity between the first non-base image and the first base image.

17. The method of claim 16, wherein selecting the value for the first weighting function comprises selecting the value that emphasizes the base image more strongly if the level of similarity between the first non-base image and the first base image is high.

18. An medical imaging system comprising:
an acquisition device;
a display device; and
a processor in electronic communication with the acquisition device and the display device, wherein the processor is configured to:
control the acquisition device to acquire image data of a periodically moving structure over more than a single physiological cycle, the image data comprising a plurality of images representing the structure at different phases of a physiological cycle;
associate phase information from the physiological cycle with the image data;
identify a base image sequence from the image data based on the phase information, the base image sequence corresponding to an integral number of physiological cycles;
identify a plurality of non-base images in the image data, where the plurality of non-base images were acquired either before or after the base image sequence during the process of said acquiring the image data of the periodically moving structure;
generate a blended image sequence, the blended image sequence comprising a start, an end, a set of blended images, an unblended portion, and a seam indicating a location in the blended image sequence where the blended image sequence transitions from the end to the start when the blended image sequence is displayed as a blended cine loop, where the blended portion of the blended image sequence is generated by blending each of the plurality of non-base images with a corresponding one of the base images according to one of a plurality of weighting functions, where the weighting function used to control the blending is selected based on a distance of the blended image from the seam, where the set of blended images reduces the appearance of the seam when the blended image sequence is displayed as the blended cine loop; and
display the blended image sequence as the blended cine loop on the display device.

19. The medical imaging system of claim 18, wherein the processor is configured to automatically identify the base image sequence.

20. The medical imaging system of claim 18, wherein the processor is configured to acquire the image data as part of a partial volume acquisition.

21. The medical imaging system of claim 18, wherein the plurality of non-base images are part of a non-base image sequence.

22. The medical imaging system of claim 21, wherein the processor is configured to use a different weighting function for blending each image of the non-base image sequence with the corresponding image from the base image sequence.

23. The medical imaging system of claim 22, wherein the processor is configured to select the different weighting function based on a distance of a corresponding image pair from a seam in the blended cine loop.

24. The medical imaging system of claim 18, wherein the medical imaging system is an ultrasound imaging system, and wherein the acquisition device comprises a probe.

* * * * *